(12) United States Patent
Westenfelder

(10) Patent No.: US 8,603,462 B2
(45) Date of Patent: Dec. 10, 2013

(54) STEM-CELL, PRECURSOR CELL, OR TARGET CELL-BASED TREATMENT OF MULTI-ORGAN FAILURE AND RENAL DYSFUNCTION

(75) Inventor: Christof Westenfelder, Salt Lake City, UT (US)

(73) Assignees: University of Utah Research Foundation, Salt Lake City, UT (US); United States of America Department of Veteran's Affairs., Washington, DC (US)

( * ) Notice: Subject to any disclaimer, the term of this patent is extended or adjusted under 35 U.S.C. 154(b) by 1337 days.

(21) Appl. No.: 10/551,317

(22) PCT Filed: Mar. 31, 2004

(86) PCT No.: PCT/US2004/009922
§ 371 (c)(1),
(2), (4) Date: Aug. 21, 2006

(87) PCT Pub. No.: WO2004/090112
PCT Pub. Date: Oct. 21, 2004

(65) Prior Publication Data
US 2007/0178071 A1    Aug. 2, 2007

Related U.S. Application Data

(60) Provisional application No. 60/459,554, filed on Apr. 1, 2003, provisional application No. 60/475,178, filed on Jun. 2, 2003.

(51) Int. Cl.
*A01N 63/00* (2006.01)
*C12N 5/0775* (2010.01)

(52) U.S. Cl.
USPC .................. 424/93.7; 424/93.21; 435/372

(58) Field of Classification Search
USPC ................. 424/93.7, 93.21; 435/372
See application file for complete search history.

(56) References Cited

U.S. PATENT DOCUMENTS

| | | | |
|---|---|---|---|
| 5,197,985 A | 3/1993 | Caplan et al. | |
| 5,226,914 A | 7/1993 | Caplan et al. | |
| 5,486,359 A * | 1/1996 | Caplan et al. | ................ 424/93.7 |
| 5,591,625 A | 1/1997 | Gerson et al. | |
| 5,643,736 A | 7/1997 | Bruder et al. | |
| 5,733,542 A | 3/1998 | Haynesworth et al. | |
| 5,736,396 A | 4/1998 | Bruder et al. | |
| 5,811,094 A | 9/1998 | Caplan et al. | |
| 5,827,740 A | 10/1998 | Pittenger | |
| 5,837,539 A | 11/1998 | Caplan et al. | |
| 5,855,619 A | 1/1999 | Caplan et al. | |
| 5,876,708 A | 3/1999 | Sachs | |
| 5,908,782 A | 6/1999 | Marshak et al. | |
| 5,908,784 A | 6/1999 | Johnstone et al. | |
| 5,942,225 A | 8/1999 | Bruder et al. | |
| 5,965,436 A | 10/1999 | Thiede et al. | |
| 6,010,696 A | 1/2000 | Caplan et al. | |
| 6,022,540 A | 2/2000 | Bruder et al. | |
| 6,030,836 A | 2/2000 | Thiede et al. | |
| 6,087,113 A | 7/2000 | Caplan et al. | |
| 6,149,906 A | 11/2000 | Mosca | |
| 6,174,333 B1 | 1/2001 | Kadiyala et al. | |
| 6,225,119 B1 | 5/2001 | Qasba et al. | |
| 6,239,157 B1 | 5/2001 | Mbalaviele | |
| 6,255,112 B1 | 7/2001 | Thiede et al. | |
| 6,261,549 B1 | 7/2001 | Fernandez et al. | |
| 6,281,012 B1 | 8/2001 | McIntosh et al. | |
| 6,322,784 B1 | 11/2001 | Pittenger et al. | |
| 6,328,960 B1 | 12/2001 | McIntosh et al. | |
| 6,342,370 B1 | 1/2002 | Connolly et al. | |
| 6,355,239 B1 | 3/2002 | Bruder et al. | |
| 6,358,702 B1 | 3/2002 | Connolly | |
| 6,368,636 B1 | 4/2002 | McIntosh et al. | |
| 6,372,494 B1 | 4/2002 | Naughton et al. | |
| 6,379,953 B1 | 4/2002 | Bruder et al. | |
| 6,387,367 B1 | 5/2002 | Davis-Sproul et al. | |
| 6,387,369 B1 | 5/2002 | Pittenger et al. | |
| 6,429,012 B1 | 8/2002 | Kraus et al. | |
| 6,482,231 B1 | 11/2002 | Abatangelo et al. | |
| 6,541,024 B1 | 4/2003 | Kadiyala et al. | |
| 6,685,936 B2 | 2/2004 | McIntosh et al. | |
| 2002/0150561 A1 | 10/2002 | Krause et al. | |
| 2004/0258670 A1 * | 12/2004 | Laughlin et al. | ........... 424/93.21 |

FOREIGN PATENT DOCUMENTS

| | | |
|---|---|---|
| AU | 2004227342 A1 | 10/2004 |
| CA | 2521217 A1 | 10/2004 |
| WO | WO-0246424 A2 | 6/2002 |
| WO | WO 03/013588 * | 2/2003 |

(Continued)

OTHER PUBLICATIONS

Imai et al. (2002) Ped. Nephrol., vol. 17, 790-794.*

(Continued)

*Primary Examiner* — Anne Marie S Wehbe
(74) *Attorney, Agent, or Firm* — Mintz Levin Cohn Ferris Glovsky and Popeo, P.C.; Ivor R. Elrifi; Christina K. Stock, Esq.

(57) ABSTRACT

Methods for the treatment of acute renal failure, multi-organ failure, early dysfunction of kidney transplant, chronic renal failure, organ dysfunction, and wound healing are provided. The methods include delivering a therapeutic amount of hematopoietic stem cells, non-hematopoietic, mesenchymal stem cells, hemangioblasts, and pre-differentiated cells to a patient in need thereof.

6 Claims, No Drawings

(56) References Cited

FOREIGN PATENT DOCUMENTS

| WO | 03105908 A2 | 12/2003 |
|---|---|---|
| WO | 2004044142 A2 | 5/2004 |
| WO | 2004090112 A2 | 10/2004 |

OTHER PUBLICATIONS

Fibbe et al. (2001) Ann. N.Y. Acad. Sci., vol. 938, 9-17.*
Japanese-English Machine Translation of WO 03/13588 (2003), Tabata et al.*
Lin et al. (May 1, 2003) J. Am. Soc. Nephrol., vol. 14, 1188-1199.*
U.S. Appl. No. 60/431,347.*
Hayakawa, J. et al.; "*Generation of a chimeric mouse reconstituted with green fluorescent protein-positive bone marrow cells: a useful model for studying the behavior of bone marrow cells in regeneration in vivo,*" Int J Hematol. Jun. 2003; 77(5):456-62. Abstract.
Examiner's First Report, Appl. No. AU2004227342, Dated Mar. 24, 2009.
Chapel et al.; "Mesenchymal stem cells home to injured tissues when co-infused with hematopoietic cells to treat a radiation-induced multi-organ failure syndrome;" *J. Gene Med* 2003; 5: 1028-1038; XP-002429830.
Gunsilius et al.; "Hematopoietic stem cells;" Biomed Pharmacother 2001: 55: 186-94; XP-002429903.
Minguell et al.; "Mesenchymal Stem Cells;" XP-002429905.
Tögel et al.; "Administered mesenchymal stem cells protect against ischemic acute renal failure through differentiation-independent mechanisms;" *Am J Physiol Renal Physiol* 289: F31-F42; 2005; XP-002429829.
Supplementary Partial European Search Report dated Apr. 18, 2007 for European Application No. EP 04 75 8676.
Abkowitz JL et al.; "*Multilineage, non-species specific hematopoietic growth factor(s) elaborated by a feline fibroblast cell line: enhancement by virus infection*;"J Cell Physiol. Apr. 1986;127(1):189-96. Abstract.
Agbulut O. et al.; "Temporal patterns of bone marrow cell differentiation following transplantation in doxorubicin-induced cardiomyopathy;" Cardiovasc Res. May 1, 2003;58(2):451-9. Abstract.
Angelopoulou M. et al.; "Cotransplantation of human mesenchymal stem cells enhances human myelopoiesis and megakaryocytopoiesis in NOD/SCID mice;" Exp Hematol. May 2003;31(5):413-20. Abstract.
Anker PS et al.; "Nonexpanded primary lung and bone marrow-derived mesenchymal cells promote the engraftment of umbilical cord blood-derived CD34(+) cells in NOD/SCID mice;" Exp Hematol. Oct. 2003;31(10):881-9. Abstract.
Ballas CB et al; "Adult bone marrow stem cells for cell and gene therapies: implications for greater use;" J Cell Biochem Suppl. 2002;38:20-8. Abstract.
Barry FP; "Biology and clinical applications of mesenchymal stem cells;" Birth Defects Res Part C Embryo Today. Aug. 2003;69(3):250-6. Abstract.
Bensidhoum M. et al.; "Homing of in vitro expanded Stro-1- or Stro-1+ human mesenchymal stem cells into the nod/scid mouse. Their role in supporting human CD34 cell engraftment;" Blood. Jan. 8, 2004 [Epub ahead of print]. Abstract.
Bonnet D.; "Biology of human bone marrow stem cells;" Clin Exp Med. Nov. 2003;3(3):140-9. Abstract.
Bron D et al.; [Mesenchymal stem cells: source, indications and perspectives] [Article in French]; Bull Mem Acad R Med Belg. 2002;157(1-2):135-45; discussion 145-6. Abstract.
Bueren JA et al; "Genetic modification of hematopoietic stem cells: recent advances in the gene therapy of inherited diseases;" Arch Med Res. Nov.-Dec. 2003;34(6):589-99. Abstract.
Burt RK; "Hematopoietic stem cell therapy for type 1 diabetes: induction of tolerance and islet cell neogenesis;" Autoimmun Rev. May 2002;1(3):133-8. Abstract.

Caplan Al et al.; "Cell-based tissue engineering therapies: the influence of whole body physiology;" Adv Drug Deliv Rev. Aug. 3, 1998;33(1-2):3-14. Abstract.
Cashman JD et al.; Mechanisms that regulate the cell cycle status of very primitive hematopoietic cells in long-term human marrow cultures. I. Stimulatory role of a variety of mesenchymal cell activators and inhibitory role of TGF-beta. Blood. Jan. 1, 1990;75(1):96-101. Abstract.
Chapel A.; "Mesenchymal stem cells home to injured tissues when co-infused with hematopoietic cells to treat a radiation-induced multi-organ failure syndrome;" J Gene Med. Dec. 2003;5(12):1028-38. Abstract.
Cheng L et al.; "*Human mesenchymal stem cells support megakaryocyte and pro-platelet formation from CD34(+) hematopoietic progenitor cells*;" J Cell Physiol. Jul. 2000;184(1):58-69. Abstract.
Deans RJ et al.; "*Mesenchymal stem cells: biology and potential clinical uses*;" Exp Hematol. Aug. 2000;28(8):875-84. Abstract.
Delwiche F et al.; "Platelet-derived growth factor enhances in vitro erythropoiesis via stimulation of mesenchymal cells;" J Clin Invest. Jul. 1985;76(1):137-42. Abstract.
Devine SM et al.; "Role of mesenchymal stem cells in hematopoietic stem cell transplantation;" Curr Opin Hematol. Nov. 2000;7(6):358-63. Abstract.
Devine SM et al; "Mesenchymal stem cells: stealth and suppression;" Cancer J. Nov.-Dec. 2001;7 Suppl 2:S76-82. Abstract.
Dooley DC et al.; "Basic fibroblast growth factor and epidermal growth factor downmodulate the growth of hematopoietic cells in long-term stromal cultures;" J Cell Physiol. Nov. 1995;165(2):386-97. Abstract.
Eaves CJ et al.; "*Regulation of hemopoietic progenitor cell proliferation*;" Behring Inst Mitt. Aug. 1988;(83):85-92. Abstract.
Fibbe WE et al; "Ex vivo expansion and engraftment potential of cord blood-derived CD34+ cells in NOD/SCID mice;" Ann N Y Acad Sci. Jun. 2001;938:9-17. Abstract.
Fibbe WE; "Mesenchymal stem cells and hematopoietic stem cell transplantation;" Ann N Y Acad Sci. May 2003;996:235-44. Abstract.
Forbes SJ et al.; "Adult stem cell plasticity: new pathways of tissue regeneration become visible.;" Clin Sci (Lond) Oct. 2002;103(4):355-69. Abstract.
Forbes SJ et al.; "Hepatic and renal differentiation from blood-borne stem cells;" Gene Ther May 2002;9(10):625-30. Abstract.
Friedenstein; *Exp. Hematol.* 4:267-74, 1976.
Poulsom R.; "Does bone marrow contain renal precursor cells?;" Nephron Exp Nephrol 2003;93(2):e53. Abstract.
Ratajczak MZ; "Stem cell plasticity revisited: CXCR4-positive cells expressing mRNA for early muscle, liver and neural cells 'hide out' in the bone marrow;" Leukemia. Jan. 2004;18(1):29-40. Abstract.
Ringe J et al.; "Stem cells for regenerative medicine: advances in the engineering of tissues and organs;" Naturwissenschaften. Aug. 2002;89(8):338-51. Epub Jul. 23, 2002. Abstract.
Tocci A. et al.; "Mesenchymal stem cell: use and perspectives;" Hematol J. 2003;4(2):92-6. Abstract.
Tuan RS et al.; "Adult mesenchymal stem cells and cell-based tissue engineering;" Arthritis Res Ther. 2003;5(1):32-45. Epub Dec. 11, 2002. Abstract.
Van Damme A et al; "Bone marrow stromal cells as targets for gene therapy;" Curr Gene Ther. May 2002;2(2):195-209. Abstract.
Yokoo T et al.; "Stem cell gene therapy for chronic renal failure;" Curr Gene Ther. Oct. 2003;3(5):387-94. Abstract.
Zhu GR et al.; [Human bone marrow mesenchymal stem cells express multiple hematopoietic growth factors] [Article in Chinese]; Zhou XY, Lu H, Zhou JW, Li AP, Xu W, Li JY, Wang CY. Abstract.
Shi C et al.; [Prospects of Research on Bone Marrow Mesenchymal Stem Cells] [Article in Chinese]; Zhongguo Shi Yan Xue Ye Xue Za Zhi. Mar. 2000;8(1):61-65. Abstract.
Chen JL et al.; [Mesenchymal stem cells suppress allogeneic T cell responses by secretion of TGF-beta1] [Article in Chinese]; Zhongguo Shi Yan Xue Ye Xue Za Zhi. Aug. 2002;10(4):285-8, abstract only.
International Search Report dated Dec. 12, 2004 from International Application No. PCT/US04/09922.

(56) References Cited

OTHER PUBLICATIONS

Examiner's Report, Appl. No. CA 2,521,217, Dated May 11, 2009.
Minguell et al., (2001), Exp. Biol. & Med., 226:507-520.
Abkowitz, J.L. et al., "Multilineage, non-species specific hematopoietic growth factor(s) elaborated by a feline fibroblast cell line: enhancement by virus infection", J. Cell Physiol. (1986), 127(1):189-96.
Agbulut O. et al., "Temporal patterns of bone marrow cell differentiation following transplantation in doxorubicin-induced cardiomyopathy", Cardiovasc. Res. (2003), 1, 58(2):451-9.
Angelopoulou M. et al., "Cotransplantation of human mesenchymal stem cells enhances human myelopoiesis and megakaryocytopoiesis in NOD/SCID mice", Exp. Hematol. (2003), 31(5):413-20.
Anker P.S. et al., "Nonexpanded primary lung and bone marrow-derived mesenchymal cells promote the engraftment of umbilical cord blood-derived CD34+ cells in NOD/SCID mice", Exp. Hematol. (2003), 31(10):881-9.
Ballas C.B. et al., "Adult bone marrow stem cells for cell and gene therapies: implications for greater use", J. Cell Biochem Suppl. (2002), 38:20-8.
Barry F.P., "Biology and clinical applications of mesenchymal stem cells", Birth Defects Res. Part C Embryo Today, (2003), 69(3):250-6.
Bensidhoum M. et al., "Homing of in vitro expanded Stro-1-or Stro-1+ human mesenchymal stem cells into the NOD/SCID mouse. Their role in supporting human CD34 cell engraftment", Blood, (2004), 103(9):3313-3319.
Bonnet D., "Biology of human bone marrow stem cells", Clin. Exp. Med. (2003), 3(3):140-9.
Bron D., "Hematopoietic stem cells: source, indications and perspectives [Article in French]", Bull Mem. Acad. R. Med. Belg. (2002), 157(1-2):135-45.
Bueren J.A. et al., "Genetic modification of hematopoietic stem cells: recent advances in the gene therapy of inherited diseases", Arch. Med. Res. (2003), 34(6):589-99.
Burt R.K., "Hematopoietic stem cell therapy for type 1 diabetes: induction of tolerance and islet cell neogenesis", Autoimmun. Rev. (2002): 1(3):133-8.
Caplan A.I. et. al., "Cell-based tissue engineering therapies: the influence of whole body physiology", Adv. Drug Deliv. Rev. (1998), 33(1-2):3-14.
Cashman J.D. et al., "Mechanisms that regulate the cell cycle status of very primitive hematopoietic cells in long-term human marrow cultures. I. Stimulatory role of a variety of mesenchymal cell activators and inhibitory role of TGF-beta", Blood, (1990), 75(1):96-101.
Cheng L et. al., "Human mesenchymal stem cells support megakaryocyte and pro-platelet formation from CD34(+) hematopoietic progenitor cells", J. Cell Physiol. (2000), 184(1):58-69.
Deans R.J. et. al., "Mesenchymal stem cells: biology and potential clinical uses", Exp. Hematol. (2000), 28(8):875-84.
Delwiche F. et. al., "Platelet-derived growth factor enhances in vitro erythropoiesis via stimulation of mesenchymal cells", J. Clin. Invest. (1985), 76(1):137-42.
Devine S.M. et. al., "Role of mesenchymal stem cells in hematopoietic stem cell transplantation", Curr. Opin. Hematol. (2000), 7(6):358-63.
Devine S.M. et. al., "Mesenchymal stem cells: stealth and suppression", Cancer J. (2001), 7 Suppl. 2:S76-82.
Dooley D.C. et. al., "Basic fibroblast growth factor and epidermal growth factor downmodulate the growth of hematopoietic cells in long-term stromal cultures;", J. Cell Physiol. (1995), 165(2):386-97.
Eaves C.J. et. al., "Regulation of hemopoietic progenitor cell proliferation", Behring Inst Mitt. (1988), 83:85-92.
Fibbe W.E. et al., "Mesenchymal stem cells and hematopoietic stem cell transplantation", Ann. N.Y. Acad. Sci. (2003), 996:235-44.
Forbes S.J. et. al., "Adult stem cell plasticity: new pathways of tissue regeneration become visible", Clin. Sci. (2002), 103(4):355-69.
Forbes S.J. et. al., "Hepatic and renal differentiation from blood-borne stem cells", Gene Ther. (2002), 9(10):625-30.
Hayakawa J. et. al., "Generation of a chimeric mouse reconstituted with green fluorescent protein-positive bone marrow cells: a useful model for studying the behavior of bone marrow cells in regeneration in vivo", Int. J. Hematol. (2003), 77(5);456-62.
Heike et al., "Stem cell plasticity in the hematopoietic system", Int. J. Hematol. (2004), 79(1):7-14.
Hirschi K.K. et. al., "Hematopoietic, vascular and ca'rdiac fates of bone marrow-derived stem cells", Gene Ther. (2002), 9(10):648-52.
Horwitz E.M., "Bone marrow transplantation: it's not just about blood anymore!", Pediatr. Transplant. (2003), 7 Suppl. 3:56-8.
Horwitz E.M., "Stem cell plasticity: the growing potential of cellular therapy.", Arch. Med. Res. (2003), 34(6):600-6.
Hughes S., "Cardiac stem cells", J. Pathol. (2002), 197(4):468-78.
Imai E et al., "Can bone marrow differentiate into renal cells?", Pediatr Nephrol (2002), 17(10):790-4.
Imasawa et al., "The potential of bone marrow-derived cells to differentiate to glomerular mesangial cells", J. Am. Soc. Nephrol (2001), 12(7):1401-9.
Ito T. et. al., "Application of bone marrow-derived stem cells in experimental nephrology", Exp. Nephrol. (2001), 9 (6):444-50.
Justesen J. et. al., "Mesenchymal stem cells. Potential use in cell and gene therapy of bone loss caused by aging and osteoporosis", Ugeskr Laeger (2001), 163(40):5491-5.
Kadereit S. et. al., "Expansion of LTC-ICs and maintenance of p21 and BCL-2 expression in cord blood CD34(+)/CD38(−) early progenitors cultured over human MSCs as a feeder layer", Stem Cells (2002), 20(6):573-82.
Kato Y. et. al., "Recipient non-hematopoietic bone marrow cells in then intestinal graft after fetal small intestinal transplantation", Pediatr. Surg. Int. (2004), 20(1):1-4.
Kim, J.H. et. al., "Co-transplantation of ex-vivo culture-expanded human mesenchymal stem cells and allogeneic hematopoietic stem cell transplantation—report of 12 cases", Blood (2002), 100(11): Abstract 4234.
Koc O.N. et. al., "Rapid hematopoietic recovery after coinfusion of autologous-blood stem cells and culture-expanded marrow mesenchymal stem cells in advanced breast cancer patients receiving high-dose chemotherapy", J. Clin. Oncol. (2000), 18(2):307-16.
Krause D.S. "Plasticity of marrow-derived stem cells", Gene Ther. (2002), 9(11):754-8.
Kucia M. et. al., "Tissue-specific muscle, neural and liver stemlprogenitor cells reside in the bone marrow, respond to an SDF-1 gradient and are mobilized into peripheral blood during stress and tissue injury", Blood Cells Mol. Dis. (2004), 32(1):52-7.
Le Blanc K., "Mesenchymal stem cells. Basic science and future clinical use [Article in Swedish]", Lakartidningen, (2002), 99(12):1318-21.
Lee K. et al., "Human mesenchymal stem cells maintain transgene expression during expansion and Differentiation", Mol. Ther. (2001), 3(6):857-66.
Mackenzie T.C. et. al., "Human mesenchymal stem cells persist, demonstrate site-specific multipotential differentiation, and are present in sites of wound healing and tissue regeneration after transplantation into fetal sheep", Blood Cells Mol. Dis. (2001), 27(3):601-4.
Majumdar M.K. et. al., "Characterization and functionality of cell surface molecules on human mesenchymal stem cells", J. Biomed. Sci. (2003), 10(2):228-41.
Maitra B. et. al., "Human mesenchymal stem cells support unrelated donor hematopoietic stem cells and suppress T-cell activation", Bone Marrow Transplant. (2004), 33(6):597-604.
Mbalaviele G. et. al., "Human mesenchymal stem cells promote human osteoclast differentiation from CD34+ bone marrow hematopoietic progenitors", Endocrinology (1999), 140(8):3736-43.
Noort W.A. et. al., "Mesenchymal stem cells promote engraftment of human umbilical cord blood-derived;" CD34(+) cells in NOD/SCID mice, Exp. Hematol. (2002), 30(8):870-8.
Orlic D., "Adult bone marrow stem cells regenerate myocardium in ischemic heart disease", Ann. N.Y. Acad. Sci. (2003), 996:152-7.
Poulsom R., "Does bone marrow contain renal precursor cells?", Exp. Nephrol. (2003), 93(2):e53.

(56) References Cited

OTHER PUBLICATIONS

Ratajczak M.Z., "Stem cell plasticity revisited: CXCR4-positive cells expressing mRNA for early muscle, liver and neural cells 'hide out' in the bone marrow", Leukemia (2004), 18(1):29-40.

Ringe J. et. al., "Stem cells for regenerative medicine: advances in the engineering of tissues and organs", Naturwissenschaften (2002), 89(8):338-51.

Tocci A. et. al., "Mesenchymal stem cell: use and perspectives", Hematol. J. (2003), 4(2):92-6.

Tuan R.S. et. al., "Adult mesenchymal stem cells and cell-based tissue engineering", Arthritis Res. Ther. (2003), 5 (1):32-45.

Van Damme A. et. al., "Bone marrow stromal cells as targets for gene therapy", Curr. Gene Ther. (2002), 2 (2):195-209.

Yokoo T. et. al., "Stem cell gene therapy for chronic renal failure", Curr. Gene Ther. (2003), 3(5):387-94.

Morigi et al. (2004), J Am Soc Nephrol, 15:1794-1804.

Examination Report, Application No. EP05757300.8, Date: Dec. 4, 2009.

Gupta et al., "A role for extrarenal cells in the regeneration following acute renal failure", Kidney International (2002), 62:1285-1290.

Ito et al., "Bone marrow is a reservoir of repopulating mesangial cells during glomerular remodeling", J Am Soc Nephrol (2001), 12:2625-2635.

Lin et al., "Hematopoietic stem cells contribute to the regeneration of renal tubules after renal ischemia-reperfusion injury", J Am Soc Nephrol (2003), 14:1188-1199.

Poulsom et al., "Bone marrow contributes to renal parenchymal turnover and regeneration", Journal of Pathology (2001), 195:229-235.

Badiavas et al., "Participation of Bone Marrow Derived Cells in Cutaneous Wound Healing", Journal of Cellular Physiology (2003), 196(2):245-250.

Bruder et al., "The Effect of Implants Loaded with Autologous Mesenchymal Stem Cells on the Healing of Canine Segmental Bone Defects", Journal of Bone and Joint Surgery (1998), 80(7):985-996.

Shumakov et al., "Mesenchymal Bone Marrow Stem Cells More Effectively Stimulate Regeneration of Deep Burn Wounds than Embryonic Fibroblasts", Bulletin of Experimental Biology and Medicine, 136(2):192-195.

Young et al., "Use of Mesenchymal Stem Cells in a Collagen Matrix for Achilles Tendon Repair", Journal of Orthopaedic Research, 16(4):406-413.

Brodsky et al. "Endothelial Dysfunction in Ischemic Acute Renal Failure: Rescue by Transplanted Endothelial Cells." *Am. J. Physiol. Renal Physiol.* 282(2002):F1140-F1149.

\* cited by examiner

STEM-CELL, PRECURSOR CELL, OR TARGET CELL-BASED TREATMENT OF MULTI-ORGAN FAILURE AND RENAL DYSFUNCTION

RELATED APPLICATIONS

This application is the National Stage of International Application No. PCT/US2004/009922 filed Mar. 31, 2004, which claims priority to U.S. Provisional Application Ser. Nos. 60/459,554, filed Apr. 1, 2003 and 60/475,178, filed Jun. 2, 2003, these references are incorporated herein in their entirety.

STATEMENT REGARDING FEDERALLY SPONSORED RESEARCH OR DEVELOPMENT

The subject matter described herein was in-part made possible by support from the Department of Veterans Affairs. The government has certain rights in the invention.

FIELD OF THE INVENTION

The present invention generally relates to methods for treating organ dysfunction, multi-organ failure and renal dysfunction, including, but not limited to acute renal failure, transplant associated acute renal failure, chronic renal failure, and wound healing. More specifically, the inventive methods use stem cells, precursor cells or organ-specific target cells and combinations thereof.

BACKGROUND OF THE INVENTION

Multi-organ failure (MOF) remains a major unresolved medical problem. MOF develops in the most severely ill patients who have sepsis, particularly when the latter develops after major surgery or trauma. It occurs also with greater frequency and severity in elderly patients, those with diabetes mellitus, underlying cardiovascular disease and impaired immune defenses. MOF is characterized by shock, acute renal failure (ARF), leaky cell membranes, dysfunction of lungs, liver, heart, blood vessels and other organs. Mortality due to MOF approaches 100% despite the utilization of the most aggressive forms of therapy, including intubation and ventilatory support, administration of vasopressors and antibiotics, steroids, hemodialysis and parenteral nutrition. Many of these patients have serious impairment of the healing of surgical or trauma wound, and, when infected, these wounds further contribute to recurrent infections, morbidity and death.

ARF is defined as an acute deterioration in renal excretory function within hours or days, resulting in the accumulation of "uremic toxins," and, importantly, a rise in the blood levels of potassium, hydrogen and other ions, all of which contribute to life threatening multisystem complications such as bleeding, seizures, cardiac arrhythmias or arrest, and possible volume overload with pulmonary congestion and poor oxygen uptake. The most common cause of ARF is an ischemic insult of the kidney resulting in injury of renal tubular and postglomerular vascular endothelial cells. The principal etiologies for this ischemic form of ARF include intravascular volume contraction, resulting from bleeding, thrombotic events, shock, sepsis, major cardiovascular surgery, arterial stenoses, and others. Nephrotoxic forms of ARF can be caused by radiocontrast agents, significant numbers of frequently used medications such as chemotherapeutic drugs, antibiotics and certain immunosuppressants such as cyclosporine. Patients most at risk for all forms of ARF include diabetics, those with underlying kidney, liver, cardiovascular disease, the elderly, recipients of a bone marrow transplant, and those with cancer or other debilitating disorders.

Both ischemic and nephrotoxic forms of ARF result in dysfunction and death of renal tubular and microvascular endothelial cells. Sublethally injured tubular cells dedifferentiate, lose their polarity and express vimentin, a mesenchymal cell marker, and Pax-2, a transcription factor that is normally only expressed in the process of mesenchymal-epithelial transdifferentiation in the embryonic kidney. Injured endothelial cells also exhibit characteristic changes.

The kidney, even after severe acute insults, has the remarkable capacity of self-regeneration and consequent re-establishment of nearly normal function. It is thought that the regeneration of injured nephron segments is the result of migration, proliferation and redifferentiation of surviving tubular and endothelial cells. However, the self-regeneration capacity of the surviving tubular and vascular endothelial cells may be exceeded in severe ARF. Patients with isolated ARF from any cause, i.e., ARF that occurs without MOF, continue to have a mortality in excess of 50%. This dismal prognosis has not improved despite intensive care support, hemodialysis, and the recent use of atrial natriuretic peptide, Insulin-like Growth Factor-I (IGF-I), more biocompatible dialysis membranes, continuous hemodialysis, and other interventions. An urgent need exists to enhance the kidney's self-defense and autoregenerative capacity after severe injury.

Another acute form of renal failure, transplant-associated acute renal failure (TA-ARF), also termed early graft dysfunction (EGD), commonly develops upon kidney transplantation, mainly in patients receiving transplants from cadaveric donors, although TA-ARF may also occur in patients receiving a living related donor kidney. Up to 50% of currently performed kidney transplants utilize cadaveric donors. Kidney recipients who develop significant TA-ARF require treatment with hemodialysis until graft function recovers. The risk of TA-ARF is increased with elderly donors and recipients, marginal graft quality, significant comorbidities and prior transplants in the recipient, and an extended period of time between harvest of the donor kidney from a cadaveric donor and its implantation into the recipient, known as "cold ischemia time." Early graft dysfunction or TA-ARF has serious long-term consequences, including accelerated graft loss due to progressive, irreversible loss in kidney function that is initiated by TA-ARF, and an increased incidence of acute rejection episodes leading to premature loss of the kidney graft. Therefore, a great need exists to provide a treatment for early graft dysfunction due to TA-ARF or EGD.

Chronic renal failure (CRF) or Chronic Kidney Disease (CKD) is the progressive loss of nephrons and consequent loss of renal function, resulting in End Stage Renal Disease (ESRD), at which time patient survival depends on dialysis support or kidney transplantation. The progressive loss of nephrons, i.e., glomeruli, tubuli and microvasculature, appears to result from self-perpetuating fibrotic, inflammatory and sclerosing processes, most prominently manifested in the glomeruli and renal interstitium. The loss of nephrons is most commonly initiated by diabetic nephropathy, glomerulonephritides, many proteinuric disorders, hypertension, vasculitic, inflammatory and other injuries to the kidney. Currently available forms of therapy, such as the administration of angiotensin converting enzyme inhibitors, angiotensin receptor blockers, other anti-hypertensive and anti-inflammatory drugs such as steroids, cyclosporine and others, lipid lowering agents, omega-3 fatty acids, a low protein diet, and optimal weight, blood pressure and blood sugar control, particularly in diabetics, can significantly slow and occasionally arrest the chronic loss of kidney function in the above conditions. The development of ESRD can be prevented in some compliant patients and delayed others. Despite these successes, the annual growth of patient numbers with ESRD, requiring chronic dialysis or transplantation, remains at 6%, representing a continuously growing medical and financial burden. There exists an urgent need for the development of new interventions for the effective treatment of CRF or CKD and thereby ESRD, to treat patients who fail to respond to conventional therapy, i.e., whose renal function continues to deteriorate. Stem cell treatment will be provided to arrest/reverse the fibrotic processes in the kidney.

Taken together, therapies that are currently utilized in the treatment of ARF, the treatment of established ARF of native kidneys per se or as part of MOF, and ARF of the transplanted kidney, and organ failure in general have not succeeded to significantly improve morbidity and mortality in this large group of patients. Consequently, there exists an urgent need for the improved treatment of MOF, renal dysfunction, and organ failure.

Very promising pre-clinical studies in animals and a few early phase clinical trials administer bone marrow-derived hematopoietic stem cells for the repair or protection of one specific organ such as the heart, small blood vessels, brain, spinal cord, liver and others. These treatments have generally used only a single population of bone-marrow stem cells, either Hematopoietic (HSC) or Mesenchymal Stem Cells (MSC), and obtained results are very encouraging in experimental stroke, spinal cord injury, and myocardial infarction. The intracoronary administration of stem cells in humans with myocardial infarction or coronary artery disease has most recently been reported to result in significant adverse events such as acute myocardial infarction, other complications and death. Peripheral administration of stem cells or the direct injection into the injured myocardium showed more favorable results both in animal and Phase I trials. MSC have been infused into patients a few weeks after they first received a bone marrow transplant in the treatment of cancers, leukemias, osteogenesis imperfecta, and Hurler's syndrome to accelerate reconstitution of adequate hematopoiesis. Effective treatment of osteogenesis imperfecta and Hurler's syndrome has been shown using MSC. Importantly, administration of a mixture of HSC and MSC, known to physiologically cooperate in the maintenance of hematopoiesis in the bone marrow, has, until now (see below) not been utilized for the treatment of any of the above listed renal disorders, MOF or wound healing.

In ARF (native kidneys, transplanted kidney), microvascular endothelial cells and proximal as well as distal tubular cells become dysfunctional and are destroyed when injured, insults that together mediate the acute loss of kidney function. Successful recovery from ARF depends directly on the repair of injured renal microvessels and tubular segments. Since both HSC and MSC possess a remarkable level of plasticity, i.e., are capable to differentiate into several non-hematopoietic cell types (neurons, heart, muscle, liver, vascular and other cells) including renal tubular and vascular endothelial cells, pre-clinical studies were begun to test the concept that the co-administration of HSC and MSC may be more renoprotective than the administration of either HSC or MSC alone, as it reproduces their mutually supportive capacity in the bone marrow. Studies demonstrated that MSC can be induced, using co-culture, conditioned media and injury models, to differentiate in vitro both into vascular endothelial and tubular cell phenotypes. In addition, syngeneic vascular endothelial cells (EC) or EC derived from MSC were tested to determine whether EC could function in rats with ARF as kidney protective renal EC precursors. Without wishing to be bound to any particular theory, the present inventor believes that microvascular dysfunction and EC injury and death are prominent mediators of inadequate renal blood flow in ARF, and that the delivery of "healthy" EC or their precursors could improve renal hemodynamics, thereby augmenting tubular cell survival, protecting renal function and hastening tissue repair. The results of these studies to date show: (1) all types of EC or EC precursors, derived from all tested sources, significantly protect renal function and improve outcome in rats with established ischemic ARF, reducing mortality from ~40% to <5%; (2) MSC administration alone results in delayed but significantly accelerated recovery of renal function; (3) HSC infusion alone shows similar or slightly less improvement in functional recovery compared to that obtained with MSC; (4) the administration of a defined mix of HSC and MSC, as discussed below, appears highly effective in the treatment of ARF, the rapid reestablishment of adequate renal function after ARF, and essential elimination of animal mortality.

In the kidney, the administration of pluripotent stem cells, derived from hematopoietic or non-hematopoietic sources, can be utilized for repair of critically damaged kidney tissues. The physical or functional loss of reno-vascular endothelial and tubular cells and thus renal function, whether occurring in acute or chronic renal failure, is a serious medical condition that will be ameliorated by the present invention. Any slowing, arrest, or reversal of the decline in renal function provided by the present invention will be enormously beneficial to the affected patients with ARF, TA-ARF, CRF, or any kidney failure-associated systemic dysfunction, MOF or wound healing.

BRIEF SUMMARY

In order to alleviate one or more shortcomings of the prior art, methods of treatment are provided herein. In accordance with the present invention, methods for the treatment of acute renal failure, multi-organ failure, and early dysfunction of kidney transplant, chronic renal failure, organ dysfunction, or wound healing are provided.

In one aspect of the present invention, a method of treatment for acute renal failure, multi-organ failure, early dysfunction of kidney transplant, chronic renal failure, organ dysfunction, or wound healing is provided. The method includes delivering a therapeutic amount of a mixture of hematopoietic stem cells and/or mesenchymal stem cells to a patient in need thereof.

In another aspect of the present invention, a method of treating acute renal failure, multi-organ failure, early dysfunction of kidney transplant, chronic renal failure, or wound healing is provided. The method includes delivering a therapeutic amount of pre-differentiated stem cells to a patient in need thereof. The cells are pre-differentiated in vitro into kidney- or other organ-specific cells.

In another aspect of the present invention, a method of treating acute renal failure, multi-organ failure, early dysfunction of kidney transplant, chronic renal failure, or wound healing is provided. The method includes delivering a therapeutic amount of hemangioblasts to a patient in need thereof.

In yet another aspect of the present invention, a method of treating kidney dysfunction is provided. The method includes delivering a therapeutic amount of non-transformed stem cells to a patient in need thereof.

In yet another aspect of the present invention, a method of treating kidney dysfunction is provided. The method includes delivering a therapeutic amount of genetically modified stem cells to a patient in need thereof.

In another aspect of the present invention, a composition is provided. The composition includes a therapeutic amount of hematopoietic stem cells and mesenchymal stem cells.

In yet another aspect of the present invention, a method of treating kidney dysfunction is provided. The method includes delivering a therapeutic amount of a stimulant of stem cell mobilization to a patient in need thereof. The stimulant mobilizes stem cells to the kidney.

DETAILED DESCRIPTION OF THE INVENTION

The present invention will utilize stem cells for the repair of damaged tissues in patients in need thereof and prevention of further injury. The term "stem cells" as used herein refers to cells having developmental plasticity that are able to produce other cell types than the cells from which the stem cells are derived. The terms "stem cells" and "pluripotent stem cells" refer to cells that are not fixed as to potential development. The stem cells of the present invention are non-embryonic in origin, preferably adult stem cells.

In one aspect of the present invention, autologous hematopoietic stem cells (HSC) or mesenchymal stem cells (MSC) are administered or, when needed, are co-administered to a patient in need thereof in defined ratios. The administration of HSC or MSC or co-administration of HSC and MSC may be used in the treatment of multi-organ failure, acute renal failure of native kidneys, ARF of native kidneys in multi-organ failure, ARF in transplanted kidneys, kidney dysfunction, organ dysfunction and wound repair. HSC and MSC may be used to treat additional disorders known to one of skill in the art. Defined ratios of HSC and MSC may be used to treat the dysfunction of other organs including transplanted organs, such as, but not limited to, lungs, liver, heart, or poorly healing wounds. Allogeneic MSC or HSC may also be administered alone or co-administered in defined ratios to be utilized as treatment, for example in multi-organ failure, all types of renal dysfunction, organ dysfunction, and to promote wound healing. The term "treatment" as used herein refers to stem cells delivered to repair an injured organ and to prevent further injury in a patient in need thereof.

The conditions identified for stem cell treatment in patients in need thereof, including, but not limited to, multi-organ failure, acute renal failure of native kidneys, ARF of native kidneys in multi-organ failure, ARF in transplanted kidneys, kidney dysfunction, organ dysfunction and wound repair refer to conditions known to one of skill in the art. Descriptions of these conditions may be found in medical texts, such as *The Kidney*, by Barry M. Brenner and Floyd C. Rector, Jr., WB Saunders Co., Philadelphia, last edition, 2001, which is incorporated herein in its entirety by reference.

ARF is defined as an acute deterioration in renal excretory function within hours or days. In severe ARF, the urine output is absent or very low. As a consequence of this abrupt loss in function, azotemia develops, defined as a rise of serum creatinine levels and blood urea nitrogen levels. Serum creatinine and blood urea nitrogen levels are measured. When these levels have increased to approximately 10 fold their normal concentration, this corresponds with the development of uremic manifestations due to the parallel accumulation of uremic toxins in the blood. The accumulation of uremic toxins causes bleeding from the intestines, neurological manifestations most seriously affecting the brain, leading, unless treated, to coma, seizures and death. A normal serum creatinine level is ~1.0 mg/dL, a normal blood urea nitrogen level is ~20 mg/dL. In addition, acid (hydrogen ions) and potassium levels rise rapidly and dangerously, resulting in cardiac arrhythmias and possible cardiac standstill and death. If fluid intake continues in the absence of urine output, the patient becomes fluid overloaded, resulting in a congested circulation, pulmonary edema and low blood oxygenation, thereby also threatening the patient's life. One of skill in the art interprets these physical and laboratory abnormalities, and bases the needed therapy on these findings.

MOF is a condition in which kidneys, lungs, liver and heart functions are generally impaired simultaneously or successively, resulting in mortality rates as high as 100% despite the conventional therapies utilized to treat ARF. These patients frequently require intubation and respirator support because their lungs develop Adult Respiratory Distress Syndrome (ARDS), resulting in inadequate oxygen uptake and CO2 elimination. MOF patients also depend on hemodynamic support, vasopressor drugs, and occasionally, an intra-aortic balloon pump, to maintain adequate blood pressures since these patients are usually in shock and suffer from heart failure. There is no specific therapy for liver failure which results in bleeding and accumulation of toxins that impair mental functions. Patients may need blood transfusions and clotting factors to prevent or stop bleeding. MOF patients will be given stem cell therapy when the physician determines that therapy is needed based on assessment of the patient.

EGD or TA-ARF is ARF that affects the transplanted kidney in the first few days after implantation. The more severe TA-ARF, the more likely it is that patients will suffer from the same complications as those who have ARF in their native kidneys, as above. The severity of TA-ARF is also a determinant of enhanced graft loss due to rejection(s) in the subsequent years. These are two strong indications for the prompt treatment of TA-ARF with the stem cells of the present invention.

Chronic renal failure (CRF) or Chronic Kidney Disease (CKD) is the progressive loss of nephrons and consequent loss of renal function, resulting in End Stage Renal Disease (ESRD), at which time patient survival depends on dialysis support or kidney transplantation. Need for stem cell therapy of the present invention will be determined on the basis of physical and laboratory abnormalities described above.

Stem cell therapy will preferably be given to patients in need thereof when one of skill in the art determines that conventional therapy fails. Conventional therapy includes hemodialysis, antibiotics, blood pressure medication, blood transfusions, intravenous nutrition and in some cases, ventilation on a respirator in the ICU. Hemodialysis is used to remove uremic toxins, improve azotemia, correct high acid and potassium levels, and eliminate excess fluid. Stem cell therapy of the present invention is not limited to treatment once conventional therapy fails and may be given immediately upon developing an injury or together with conventional therapy.

Monitoring patients for a therapeutic effect of the stem cells delivered to a patient in need thereof and assessing further treatment will be accomplished by techniques known to one of skill in the art. For example, renal function will be monitored by determination of blood creatinine and BUN levels, serum electrolytes, measurement of renal blood flow (ultrasonic method), creatinine and inulin clearances and urine output. A positive response to therapy for ARF includes return of excretory kidney function, normalization of urine output, blood chemistries and electrolytes, repair of the organ and survival. For MOF, positive responses also include improvement in blood pressure and improvement in functions of one or all organs.

In another aspect of the present invention, bone-marrow derived or stem cells derived from other organs may be used to treat critically damaged kidney tissues and to prevent damage to kidney tissue in patients at risk for developing kidney damage. A single stem cell population or combinations of stem cell populations or stem cells that are pre-differentiated into kidney-specific precursor cells (e.g., tubular, vascular endothelial and glomerular cells, etc.) may be used to treat or prevent kidney damage.

Stem cells may be utilized to effectively repopulate dead or dysfunctional kidney cells because of the "plasticity" of stem cell populations. The term "plasticity" refers to the phenotypically broad differentiation potential of cells that originate from a defined stem cell population. Stem cell plasticity can include differentiation of stem cells derived from one organ into cell types of another organ. "Transdifferentiation" refers to the ability of a fully differentiated cell, derived from one germinal cell layer, to differentiate into a cell type that is derived from another germinal cell layer.

It was assumed, until recently, that stem cells gradually lose their pluripotency and thus their differentiation potential during organogensis. It was thought that the differentiation potential of somatic cells was restricted to cell types of the organ from which respective stem cells originate. This differentiation process was thought to be unidirectional and irreversible. However, recent studies have shown that somatic stem cells maintain some of their differentiation potential. For example, hematopoietic stem cells are able to transdifferentiate into muscle, neurons, liver, myocardial cells, and kidney. It is possible that as yet undefined signals that originate from injured and not from intact tissue act as transdifferentiation signals.

The present invention will utilize pluripotent stem cell populations to treat renal dysfunction and other organ dysfunction. Stem cells, including HSC, MSC, cells derived from MSC by pre-differentiation (organ-specific progenitor cells of target organs) will be used, alone or in combinations thereof, in order to augment the kidney's autoprotective capacity and to support and boost the repair processes in patients with renal dysfunction and other organ dysfunction. Stem cells used in the present intervention express receptors that, when activated by chemokine signals that emanate from sites of injury in the damaged organs, result in the homing of stem cells to these injury sites. The administration of a single cell type or mixes thereof results in the localized delivery to and accumulation of stem cells at the sites of injury. Since stem cells express renotropic survival factors, anti-inflammatory cytokines, vasoactive and other beneficial factors, these are released in the microenvironment of the injury sites in the kidney or other organs. The local levels of protective humoral factors are optimized and immediate beneficial actions on renal and other organ function are elicited. In subsequent steps, delivered stem cells and other cells gradually integrate as progressively differentiated target cells into the injured tubular epithelium and/or endothelium, and directly participate in the cellular repair processes. The pluripotent stem cell populations used to protect and repair the dysfunctional kidney and other organs may be derived from hematopoietic or mesenchymal stem cells, as hemangioblasts, as EC progenitors, or from other organs such as kidney, liver, muscle, or fat. Other cells and organs such as umbilical cord blood or cells may provide a source of stem cells to protect and repair dysfunctional kidneys and other organs. The term "non-transformed" as used herein refers to stem cells that have not been genetically modified with exogenous DNA or RNA.

In one embodiment of the present invention, the pluripotent stem cell population is derived from HSC. The HSC are derived from the bone marrow or peripheral blood, preferably the bone marrow. The HSC are isolated from a healthy and compatible donor or the patients themselves by techniques commonly known in the art. The HSC population may be enriched for pluripotent HSC using fluorescence activated cell sorting (FACS) or other methods. The pluripotent HSC may be enriched by FACS by selecting for "c-kit" positive, "sca-1" positive and "lin negative" cells. "c-kit" and "sca-1" cells are known to one of skill in the art as being receptors known to be on the surface of stem cells. A "lin negative" cell is known to one of skill in the art as being a cell that does not express antigens characteristic of specific cell lineages and thus is more primordial, pluripotent and capable of self-renewal. The HSC may be CD 34 positive or negative. Any method known to one of skill in the art may be used to enrich the population of pluripotent stem cells from the whole population of bone marrow cells, and, if necessary, cryopreserve them until needed for therapy.

Alternatively and time permitting, autologous HSC may be obtained from the peripheral blood using routine HSC mobilization protocols known to one of skill in the art with repeated leukapheresis. HSC may be enriched by FACS, and preserved until use. Mobilization of HSC into the peripheral circulation is accomplished by the daily administration of G-CSF alone or in conjunction with cytoxan or SCF. Doses of G-CSF, cytoxan and SCF for mobilization of HSC known to one of skill in the art. Mobilization doses, by way of example, may be the same doses used in the treatment of autologous bone marrow transplant patients. The resultant increase in peripheral leukocytes is paralleled by an increase in circulating HSC numbers which are collected by repeated leukapheresis. This "slower" approach of collecting HSC may be best suited for those patients who are scheduled to undergo an elective high risk surgery, i.e., patients in whom there is sufficient time to collect HSC in this fashion, and if used in combination with MSC, while their MSC are conventionally obtained from their bone marrow aspirate (see below).

MSC for administration preferably are derived from bone marrow aspirates that are placed into sterile culture in vitro. MSC from the bone marrow aspirates adhere to the bottom of a culture dish while essentially all other cell types remain in suspension. (Friedenstein, *Exp. Hematol.* 4:267-74, 1976). After discarding the non-adherent cells, MSC will grow and expand in culture, yielding a well defined population of pluripotent stem cells. After expansion in vitro, collected MSC may be further depleted of CD 45 positive cells, by FACS, to remove residual macrophages or other hematopoietic cell lineages prior their administration to the patient. MSC may be derived from the patient, from a compatible donor, or from a blood group compatible but allogeneic donor, exploiting in the latter case the immunomodulating capacity of MSC (see below). Donor stem cells may be used from a donor having similar compatibility as defined for the organ transplantation, known to one skilled in the art. Since MSC can be expanded in vitro, the treatment regimen with MSC can be easily repeated in order to further augment the cellular repair processes in the injured kidney. Any method known to one of skill in the art may be used to enrich the population of pluripotent MSC from the whole population of bone marrow cells, and, if necessary, cryopreserve them until needed for therapy.

Any donor can be used as a source of stem cells. Preferably, autologous stem cells are used since they eliminate concerns regarding immune tolerance. Additionally, by way of example, repetitive administrations of autologous MSC and HSC are possible.

MSC may also be used (see above). MSC have been shown to suppress the T-cell response, remaining immunomodulating even after differentiation into various cell types. MSC do not elicit an immune response that would result in their rejection by the donor. Suppression of the MSC response makes MSCs suitable as a first line intervention in patients in need thereof, requiring only assurance of blood group compatibility between MSC donor and recipient. Reasons for administering allogeneic MSC include:

(a) Suitability, despite being allogeneic cells, for immediate administration to a blood group compatible patient in need thereof. This is based on the inherent immunomodulating capacity that MSC and MSC-derived cells possess. MSC may be collected and saved for "off the shelf" use to provide an immediate source of cells for infusion when needed. Autologous MSC, in contrast, require more time for collection, enrichment and expansion of the cells and are not immediately available. Immediate availability of MSC is significant in patients with the most severe forms of ARF and MOF.

(b) Bone marrow in a patient in need of stem cell therapy may be a poor source of adequate numbers of stem cells. The patient may have received bone marrow toxic drugs or radiation or may have bone marrow cancer, thereby making the patient's own MSC unusable.

(c) A patient may refuse or may not be able to consent to the harvesting of his/her own bone marrow cells.

(d) Bone marrow-derived stem cells from a compatible living-related or unrelated donor of a solid organ may be of superior quality and quantity compared to the recipient's own stem cells.

(e) Bone marrow-derived stem cells alone from a compatible living donor of bone marrow only, and not a solid organ, may be of superior quality and quantity compared to that of the recipient's own stem cells.

(f) The immediate treatment with allogeneic MSC and/or cells derived therefrom by pre-differentiation, provides additional time to harvest and process the patient's own stem cells for subsequent treatments that may be needed.

Co-administration of MSC and HSC for a therapeutic dose of stem cells includes simultaneous administration of MSC and HSC, administration of MSC followed by administration of HSC and administration of HSC followed by administration of MSC. For additional therapeutic doses, the time interval between the sequential or repeated administration of HSC and/or MSC, respectively, is generally, if utilized, 1-2 days or a few weeks, depending on the responses that are obtained or expected. The stem cells may be delivered to the patient as a single population or together as mixed populations given in a single dose. The mixed populations of cells may include, but are not limited to any of the stems cells, including HSC, MSC, pre-differentiated stem cells, hemangioblasts, tubular cells, endothelial cells and combinations thereof. The stem cells may also be delivered to the patient sequentially. A dose of stem cells may also be delivered simultaneously or sequentially with a stem cell mobilization factor.

In certain embodiments, a therapeutically effective dose of stem cells is delivered to the patient. An effective dose for treatment will be determined by the body weight of the patient receiving treatment, and may be further modified, for example, based on the severity or phase of the kidney or other organ dysfunction, for example the severity of ARF, the phase of ARF in which therapy is initiated, and the simultaneous presence or absence of MOF. Preferably, about 0.01 to about $5 \times 10^6$ cells per kilogram of recipient body weight will be administered in a therapeutic dose, more preferably about 0.02 to about $1 \times 10^6$ cells per kilogram of recipient body weight will be administered in a therapeutic dose. The number of cells used will depend on the weight and condition of the recipient, the number of or frequency of administrations, and other variables known to those of skill in the art. For example, a therapeutic dose may be one or more administrations of the therapy. A subsequent therapeutic dose may include a therapeutic dose of HSC and MSC, HSC alone, or MSC alone.

The ratio of HSC to MSC for administration for treatment may be greater than about 3:1, greater than about 4:1, greater than about 5:1, greater than about 6:1, greater than about 7:1, greater than about 8:1, less than about 8:1, less than about 7:1, less than about 6:1, less than about 5:1, less than about 4:1, less than about 3:1, about 1:1, more preferably in the range of about 3:1 to about 8:1, most preferably about 5:1. Different ratios from those above may prove more effective at certain stages of ARF, e.g. early vs. late after onset. Different ratios may be used for treatment of different or more complex disorders, including MOF. Ratios of may be about 0.1:1 to about 50:1, depending on the disease being treated.

The therapeutic dose of stem cells will be administered in a suitable solution for injection. Solutions are those that are biologically and physiologically compatible with the cells and with the recipient, such as buffered saline solution or other suitable excipients, known to one of skill in the art. The stem cells will be delivered at rate known to one of skill in the art.

In another aspect of the present invention, the cellular repair processes in ARF or MOF may be significantly accelerated when the cells administered to the patient are pre-differentiated in vitro from HSC and/or MSC, as described above. Administration of vascular endothelial cells exerts renoprotective effects in ischemic ARF. HSC and MSC can differentiate into both renal tubular and vascular endothelial cells, described in Example 13, and into glomerular cells. The cellular repair processes may be further accelerated when administered cells are pre-differentiated in vitro (from HSC and MSC) to precursor cells, mature endothelial, renal tubular or cells of other organs. Using pre-differentiated cells, an injury of kidney or other organs may be organ- and cell-specifically treated. Organ injury, including microvascular and parenchymal injury, is associated with a significant level of HSC mobilization. In both multi-organ failure and ARF, the low level mobilization of HSC may be inadequate to effectively aid in the protection and repair of severely injured organs. Therefore, replacement of vascular endothelial cells, derived from HSC and/or MSC, combined with organ-specific pre-differentiated renal or other parenchymal cells may be highly effective in improving organ function and patient/animal survival in MOF. Cells for administration for treatment of MOF will be chosen based on the organ exhibiting the most life threatening dysfunction.

In another aspect of the present invention, autologous or allogeneic hemangioblasts, a subgroup of HSC and a common stem cell for both blood and blood vessel cells may be used. Hemangioblasts may be selected by FACS and used for the treatment of MOF, acute renal failure of native kidneys, ARF of native kidneys in multi-organ failure, and ARF in transplanted kidneys and failure of transplanted organs. Ischemic injury of various organs results in the spontaneous appearance of hemangioblasts through their mobilization from the bone marrow into the peripheral circulation. Human hemangioblasts express a characteristic cell surface antigen (CD 133 or AC 133), often in conjunction with CD 34, a common stem cell marker, allowing their enrichment with FACS sorting. In mice and rats, vascular endothelial cell precursors or hemangioblasts express the KDR receptor for Vascular Endothelial Growth Factor (VEGF), also facilitating enrichment by FACS sorting. Upon differentiation into endothelial or hematopoietic cells, CD 133 and KDR expression disappears. Hemangioblasts are capable of supporting both vasculogenesis/angiogenesis and hematopoiesis. These characteristics may be particularly desirable when there is severe vascular injury of the kidneys and other organs, and poor wound healing.

In another embodiment of the present invention, the pluripotent stem cells may be derived from non-hematopoietic sources such as umbilical cord blood or other tissue sources, such as the liver, muscle, or fat, or any tissue suitable as a source of pluripotent stem cells. The non-hematopoietic stem cells may be enriched in vitro and then administered to the patient as described above for the hematopoietic or mesenchymal stem cells. Non-hematopoietic stem cells may be used to treat patients having ARF, TA-ARF, or CRF.

In another embodiment of the present invention, the patient's own stem cells may be used to treat kidney dysfunction by mobilizing endogenous stem cells from the bone marrow. The stem cells may be mobilized with granulocyte-colony stimulating factor (G-CSF), and/or stem cell factor (SCF), granulocyte-macrophage colony-stimulating factor (GM-CSF), macrophage colony-stimulating factor (M-CSF), interleukin-1 (IL-1), interleukin-2 (IL-2), interleukin-3 (IL-3), interleukin-4 (IL-4), interleukin-6 (IL-6), interleukin-7 (IL-7), interleukin-8 (IL-8), interleukin-11 (IL-11), interleukin-12 (IL-12), Flt3-L, TPO and EPO, or any stem cell mobilization factor known to one skilled in the art. A therapeutic dose of a stem cell mobilization factor is a dose that increases the number of circulating stem cells by about 100 fold or greater, as assessed by the number of CD 34 positive cells in the circulation. Treatment of patients with stem cell mobilization factors results in the mobilization and transfer of hematopoietic and non-hematopoietic stem cells into the circulating blood. Thus, the blood that perfuses the kidneys or other injured organs is enriched with stem cells that are immediately available to protect kidney tubular and vascular endothelial cell functions and survival and that can subsequently physically replace cells that are damaged or destroyed due to ischemic or toxic insults to the kidney and other organs. Since injured organs, unlike intact organs, generate homing signals via activation of their cognate receptors that attract stem cells, this form of therapy is optimally focused on the protection and repair of a damaged kidney or other organ. A preferred stem cell mobilization factor does not simultaneously increase peripheral neutrophil numbers, causing granulocytosis, when the stem cells are mobilized for treatment of a patient having kidney or other organ injury. Studies have demonstrated that the marked granulocytosis that is associated with stem cell mobilization protocols that use G-CSF plus SCF or cyclophosphamide causes significant worsening of morbidity and mortality in animals with ARF and must thus be avoided. However, G-CSF and SCF or cyclophosphamide may be used to mobilize and procure stem cells in a patient with normal renal function in preparation for undergoing a major operation or therapy that puts the patient at high risk for ARF or MOF and administered if necessary if ARF or MOF develops. Increased neutrophils in normal patients do not have the same adverse effects as in patients with organ injury.

In Pre-Clinical Studies, several methods are used to track administered HSC, MSC, and EC in the kidney and other organs such as the liver, spleen, lungs, bone marrow, heart or brain. Cell tracking systems are used in which HSC, MSC and EC are labeled with vital dyes prior to administration. These vital dyes, i.e., dyes that have no harmful effect on living cells, allow the precise location of administered HSC, MSC and EC in the kidney or any organ, using techniques commonly known in the art. Another system that is utilized to track administered cells in experimental models uses HSC, MSC and EC from syngeneic animals that are transgenic for human Placental Alkaline Phosphatase (hPAP) or enhanced Green Fluorescent Protein (eGFP). The administered HSC, MSC and EC from transgenic donor animals can be readily identified in wild-type recipients of the same animal strain, using techniques commonly known in the art for identifying cells expressing hPAP or eGFP. HSC, MSC and EC derived from a male animal or male human donor, and when these are administered to a female animal or female human recipient may also be tracked. The presence of the male "Y" chromosome in the donor cells that are engrafted in the recipient's target organs or found in the circulation can be specifically identified in solid organs by Fluorescent In Situ Hybridization (FISH assay), and in general by RT-PCR and immunocytochemistry.

Post-infusion differentiation of HSC, MSC and EC into kidney-specific or other defined cells of injured organs may also be confirmed in pre-clinical studies using the tracking systems. For example, in the kidney, demonstration that the infused HSC, MSC and EC have differentiated into the renal cell type that needs to be reconstituted is accomplished by assaying for the de novo expression of cell markers that are specific for distinct kidney cell types, e.g., proximal tubular, microvascular endothelial and glomerular cells, respectively. This double labeling technique, i.e., cell tracking and proof of differentiation into organ-specific target cells, provides conclusive evidence as to the origin (HSC, MSC and EC) and kidney-specific phenotype (proximal tubular, vascular endothelial or glomerular cells) that these cells have differentiated into, respectively. Suitable differentiation markers for proximal tubular phenotype are megalin and aquaporin-1, and others. Suitable markers for vascular EC phenotype are CD31 (Pecam-1), von Willebrandt Factor, eNOS, VEGF-Receptor 2, dil-Ac-LDL uptake, and others.

In the bone marrow, as well as in long-term in vitro cultures, MSC support growth of HSC and HSC interact with MSC. Both cell types are capable of differentiation, to a variable degree, into non-hematopoietic cell types, including renal, vascular, neuronal, myocardial, hepatic and others. Co-administration of these mutually supportive MSC and HSC conceptually reproduces the situation in the bone marrow, potentially facilitating more efficient homing, engraftment and differentiation of these cells into those that are dysfunctional or destroyed in ARF, i.e., delivering humoral factors directed by homing signals to the sites of injury that augment cell survival, improve local perfusion, and reduce inflammation, and contributing to the repair of microvascular and tubular injuries.

Microenvironmental changes that are created by vascular and tubular cell injury in ARF generate homing and differentiation signals for stem cells, and signals that guide and regulate the repair processes, thought to be primarily carried out by surviving renal cells. Administration of MSC and/or HSC, through transient but immediately active mechanisms, protects organ function and augments organ repair. These cells can locally release growth factors and cytokines such as Hepatocyte Growth Factor (HGF), Vascular Endothelial Growth Factor, Nitric Oxide, and others, which are known to exert powerful renoprotective actions. Para- and endocrine intrarenal release of growth factors and cytokines may be particularly beneficial in the early phase of ARF treatment with stem cells, since growth factors can enhance cell survival and stimulate proliferation of renal cells in ARF. Subsequent progressive differentiation of MSC and HSC into kidney-specific cell types engrafted at sites of renal injury, will directly contribute to or undertake the necessary cellular repairs.

In addition to providing kidney precursor cells in the treatment of ARF, administered MSC and/or HSC may be utilized for therapeutic gene delivery. MSC, HSC, EC, hemangioblasts or mixes thereof may be genetically engineered or modified by transfection in vitro to augment the expression of therapeutically beneficial genes and/or to suppress the expression of harmful genes prior to administration of cells to a patient. For cell transfections, methods known to one of skill in the art will be used. See e.g. Sambrook et al. Molecular Cloning: A Laboratory Manual (current edition). The transfected genes may include genes whose products are known to support cellular survival, stimulate cell migration and proliferation, to exert anti-inflammatory and anti-thrombotic actions and to improve intrarenal hemodynamics, and other organ protective effects. The activity of such beneficial genes delivered in this fashion may be placed under the control of drug-sensitive promoters that allow both controlled activation and inactivation of these genes. Genetically engineered cells may be used in treatment of kidney dysfunction, as well as in MOF, organ dysfunction, and wound repair. The term "genetically modified" as used herein refers to stem cells that have been genetically modified with exogenous DNA or RNA. The term "transformed" refers to cells that have acquired malignant characteristics. The term "non-transformed" refers to stem cells that have not been genetically modified with exogenous DNA or RNA.

Defined patient populations are expected to benefit from the administration of HSC, MSC, EC, hemangioblasts or combinations thereof. For example, patients with treatment-resistant (hemodialysis, parenteral nutrition, antibiotics, ICU care) forms of ARF alone or in the setting of MOP or multi-organ dysfunction, have only a small survival chance and will therefore be prime candidates for this cell-based treatment. Patients at highest risk for or who are about to develop the most severe form of treatment-resistant ARF would be prepared for HSC, MSC, EC, hemangioblasts or combinations therapy by obtaining their bone marrow aspirate and preparing HSC, MSC, EC, or hemangioblasts as above. Blood group matched, allogeneic MSC or precursor EC or tubular or other cells derived from MSC by pre-differentiation would be used as the first intervention in these patients. Time permitting and if no clinical contraindications exist, HSC may be obtained with a stem cell mobilization and leukapheresis protocol as detailed above, or by the use of a mobilizing factor such as erythropoietin that only enhance the number of peripheral stem cells and EC precursor cells, and not neutrophils that may be harmful to the patient with ARF or MOF. Time permitting and if needed, autologous MSC may be obtained from the patients' bone marrow, placed in suitable culture for enrichment and expansion. These autologous MSC would be administered following the initial administration of allogeneic MSC and/or precursors, when needed. The prepared autologous stem cells can be cryopreserved and administered when warranted by a poor response to allogeneic MSC or the development of life threatening deterioration in the function of kidneys and/or other vitally important organs, i.e., complications that would warrant additional MSC treatments.

Trauma or surgical patients scheduled to undergo high risk surgery such as the repair of an aortic aneurysm, may also benefit from prophylactic HSC, MSC, and hemangioblast collection and preparation, from MSC, of precursor EC or tubular or other cells, prior to major surgery. In the case of poor outcome, including infected and non-healing wounds, development of MOF post surgery, the patient's own HSC, MSC, and hemangioblast or MSC-derived target cells that are cryopreserved may be thawed out and administered as detailed above. Patients with severe ARF affecting a transplanted kidney may either be treated with HSC, MSC, and hemangioblast or MSC-derived precursor cells from the donor of the transplanted kidney (allogeneic) or with cells from the recipient (autologous). Rejection of both allogeneic HSC or hemangioblasts as well as that of the transplanted kidney or other organ graft would be prevented by the concomitant administration of immunosuppressive agents such as drugs and immune modulating MSC. Blood group matched, allogeneic MSC are an immediate treatment option in patients with TA-ARF and for the same reasons as described in patients with ARF of their native kidneys.

In another aspect of the present invention, MSC and/or HSC may be co-administered in defined ratios for the treatment of MOF and the ARF that always develops in patients with MOF. MSC and/or HSC therapy, in the setting of MOF, contributes to and augments the defense and repair processes of all significantly injured organs, i.e., kidneys, lungs, heart, liver, etc. It has been shown that the administration of bone marrow-derived stem cells to animals with damage of very different organs, e.g., experimental stroke or neurotoxic insult models, spinal cord injury, myocardial infarction, liver injury, and ARF data described below, results in protection and repair of individually targeted organs. Co-administration of MSC and HSC and/or other cells, as described in this invention, may thus represent an intervention that can effectively boost both a patient's capacity to survive the immediate deleterious consequences of MOF and to subsequently carry out repair of organs that are damaged in the context of MOF.

In another aspect of the present invention, MSC, HSC, precursor cells derived from MSC or the bone marrow or circulation, or pre-differentiated cells specific to the target organ and combinations thereof may be administered in defined ratios for the treatment of ARF in the transplanted kidney. MSC have been shown to act in an immunomodulatory manner, i.e., they are able to enhance a recipient's tolerance for an allograft (see above). Administration of bone marrow-derived allogeneic stem cells from the kidney donor results in generalized microchimerism in the kidney recipient, also known to lead to enhanced graft tolerance. Co-transplantation of MSC and HSC may have immediate reno-protective effects, as in ARF of native kidneys (see above), thereby ameliorating or preventing EGD or TA-ARF, as well as diminishing the late consequences of severe EGD (increased graft rejection rates) by induction of enhanced graft tolerance through several immune-modulatory mechanisms (see above).

Administration of autologous HSC, MSC, MSC-derived precursor cells or organ-specific target cells and combinations thereof obtained in advance to the kidney transplant from the kidney recipient, may permit significant replacement of donor renovascular endothelial cells with those of the recipient. Replacement of donor renovascular endothelial cells that are lost in EGD with endothelial cells prophylactically obtained from the recipient, or derived by pre-differentiation from autologous MSC and/or HSC, may thus reduce the immunogenicity of the donor kidney, since vascular endothelial cells represent the most immediate barrier between the recipient's blood elements, including cells and antibodies that mediate vascular/cellular rejection, and the parenchymal cells of the implanted kidney. Replacement of a significant percentage of the donor kidney's vascular endothelial cells with endothelial cells derived from the recipient, the recipient's MSC and/or HSC will reduce the number of "foreign" vascular endothelial cells present in the transplant, creating a "reno-vascular microchimerism".

Stem cells are administered to the patient by infusion intravenously (large central vein such vena cava) or intra-arterially (via femoral artery into supra-renal aorta). Any delivery method for stem cells, commonly known in the art, may be used for delivery of the administered MSC, HSC, hemangioblasts or precursor cells obtained by pre-differentiation from MSC as defined above.

In certain embodiments, a therapeutically effective dose of stem cells and/or a therapeutically effective dose of a stem cell mobilization factor(s) that does not cause a rise in peripheral neutrophils are delivered to the patient with ARF, TA-ARF, or MOF. An effective dose for treatment will be determined by the body weight of the patient receiving treatment, the patient's response to these treatments, comorbidities and severity of disease. A therapeutic dose may be one or more administrations of the therapy. Delivery of the stem cells may be by mobilization of endogenous stem cells, or by intravenous or intra-arterial infusion.

In another aspect of the present invention, the above delineated technologies may be established in tertiary care centers world wide. In analogy to company-owned in-hospital and free-standing hemodialysis units, multidisciplinary "Stem Cell Nephroplasty Teams" or "Cell Therapy Teams" could be owned and operated by international Health Care Equipment and Service companies that would also produce and sell their or other companies' kits and materials used for the harvesting, purification, culturing, differentiation, cryopreservation, thawing, quality control and administration of stem cells or stem cells that are pre-differentiated in vitro to patients at high risk for ARF or multi-organ failure (Prevention), and to patients with established ARF or multi-organ failure (Treatment). Physicians (Nephrologists, Intensivists, etc.) who care for this group of patients would order respective cell-based services, and these specialized teams would provide the requested treatment.

In a preferred embodiment of the present invention, the stem cells (HSC, MSC, hemangioblasts, precursor cells) utilized for these treatments will be "harvested" and prepared on site, i.e., in the hospital by a specialized team or in free-standing "Stem Cell Donation Centers" from the following donors: 1) a patient will donate his/her own bone marrow for treatment of his/her own ARF or organ failure, i.e., autologous stem cells; 2) a blood group and tissue-type identical allogeneic donor; 3) a blood group compatible but not tissue-type identical allogeneic donor as source of allogeneic MSC and precursor cells derived from these MSC. Stem cells from these donor groups are administered when ARF develops in the native or transplanted kidney or when organ failure develops in another transplanted organ (heart, liver, lungs, pancreas, islet cells, and others). In this setting, harvesting of solid organs from a cadaveric donor (kidneys, liver, heart etc.) would be complemented by the simultaneous harvesting of the cadaveric or living related donor's bone marrow-derived stem cells, by that very same specialized team (as above). Since the solid organs to be transplanted are always screened for compatibility with prospective recipients, the simultaneously harvested stem cells would thus be automatically identified as being compatible with the recipient of any of the solid organs. Thus, keeping these stem cells available by cryopreservation, makes them readily available for developing treatment needs following transplantation of the solid organs into multiple recipients (kidneys, heart, liver, etc.). The immunosuppressive drugs needed to prevent rejection of a transplanted organ (kidney, heart, liver, lungs, pancreas, etc.) would simultaneously serve to prevent the rejection of administered, non-tissue type identical stem cells. This effect would be further enhanced by the immune modulating actions of MSC, if co-administered. As used herein, the terms "harvesting and administering" may include the following: harvesting, processing, enriching, characterizing, cyropreserving, thawing, performing quality control, and administering.

In another embodiment of the present invention, the homing signals and mechanisms that direct the delivery of stem cells to the sites of injury in the native or transplanted kidney with ARF, with CRF or to other damaged organs in MOF or to poorly healing wounds may be utilized. Injured organs upregulate expression of SDF-1 alpha and SDF-1 beta, chemokines that attract stem cells and precursor cells expressing CXCR-4, the receptor for SDF-1. At the injury site, locally produced SDF-1 results in the generation of a concentration gradient. Consequently, the SDF-1 concentration is highest at the site of tissue injury and determines thus the direction and intensity of a stem cells homing response. The stem cells and precursor cells of the present invention may be genetically modified to optimize the expression of CXCR-4 on their cell surface to thereby increase the homing response of the cells to the injury site. Similarly, additional receptors present on stem cells known to one of skill in the art, i.e., receptors that additionally mediate the homing of stem cells to injured tissues may be over-expressed by transfection in the stem cells, precursor cells, or target cells of the present invention. Transfection methods known to one of skill in the art may be used to genetically modify the cells to optimally home to the site of injury.

In another embodiment of the present invention, the bone marrow stem cell mobilization signals and mechanisms that emanate from a kidney with ARF or from other injured organs can be augmented for therapeutic indications by the administration of stem cell mobilization factors known to those skilled in the field. In this fashion the spontaneous stem cell mobilization response that appears inadequate to protect severely injured kidneys or other organs can be augmented by suitable factors such as erythropoietin.

EXAMPLES

Example 1

Determine the Relative Renoprotective Potency of HSC, MSC, Precursor Vascular Endothelial or Tubular Cells Derived from MSC by Pre-Differentiation, Hemangioblasts, of Fully Differentiated Vascular Endothelial Cells, and of Fibroblasts Administered to Rats with ARF In experiments, adult Sprague-Dawley or Fisher 344 rats (male or female) were studied. Ischemia/reperfusion-type of ARF ("ischemic ARF") is induced in anesthetized rats by timed clamping of both renal pedicles, thereby interrupting the blood supply to the kidneys causing an "ischemic" insult that results in acute loss of kidney function, i.e., ARF. A model of severe ARF in rats used 45 minutes of bilateral renal ischemia, resulting in a rise in serum creatinine to 3.5-5.0 mg/dL, a glomerular filtration rate of <15% of normal, and a mortality of 50% at 72 hrs post reflow. Histological examination of the kidneys from this severe ARF model shows wide spread tubular necrosis, apoptosis and severe vascular congestion with accumulation of inflammatory cells in the corticomedullary junction. A moderate ARF model in rats used 35 minutes of bilateral renal ischemia, resulting in a rise in serum creatinine level to 1.5-2.5 mg/dL at 24 hours post reflow, and a mortality of <10% at 72 hours post reflow. Histological examination of the kidneys from this moderate ARF model demonstrates more limited tubular necrosis, apoptosis and modest vascular congestion with lower level accumulation of inflammatory cells in the corticomedullary junction. These models of ARF very closely resemble the most common and most serious forms of ARF encountered in patients with shock, sepsis, trauma, after major cardiac or vascular surgery, etc.

The relative renoprotective potency of various SC and cell treatment protocols was tested by infusing intravenously jugular, femoral or tail vein) or intra-arterially (into suprarenal aorta via carotid or femoral artery) syngeneic HSC alone, MSC alone, precursor cells of endothelial or tubular phenotype obtained by pre-differentiation of MSC, hemangioblasts, obtained from HSC by FACS sorting, mature vascular EC and, as cell control, fibroblasts either immediately or 24 hrs after induction of severe or modest ARF, respectively. The total number of each cell type administered in all studies was about $10^5$ to $10^6$ cells/animal. Control animals were sham operated and were injected either with vehicle or fibroblasts alone.

Renal function in all animal groups was monitored, as in patients, by determination of blood creatinine and BUN levels, serum electrolytes, measurement of renal blood flow (ultrasonic method), creatinine and inulin clearances and urine output. Overall animal outcome was assessed by determination of weight loss, hemodynamics (blood pressure), and survival. After sacrifice of control and cell-treated animals with ARF and shams, kidneys were examined for the degree of histological injury (cell apoptosis, necrosis, vascular congestion and injury, inflammatory cell infiltrates) and repair (mitogenesis, redifferentiation of cells, decongestion, etc.), intrarenal localization of the administered HSC/MSC (as discussed above, the administered HSC/MSC are tagged for tracking purposes), and their integration and differentiation into renal cells. Selected animals in the various groups were followed for up to 28 days after start of study.

The following observations from the experiments using the rat model of ARF were made: (1) all types and sources of administered EC (precursors from MSC, mature EC) and hemangioblasts significantly protect renal function and improve outcome in rats with ischemic ARF, both when given immediately or 24 hrs post reflow. Protection in all groups was significant both in animals with severe and modest ARF, the cell type that appears most protective when administered immediately after reflow of the ischemic kidneys appears the EC phenotype, however the subsequent renoprotective effects obtained with the administration of all individual cell types were comparable. In addition, mortality in severe ARF is reduced from ~40% to <5%; (2) MSC administered alone result in delayed but significantly accelerated recovery of renal function; (3) HSC infused alone show similar or slightly less improvement in functional recovery compared to that obtained with MSC or EC; (4) fibroblast infusion had no effect on renal function in rats with ARF or shams. Obtained functional protection and return of function shows good correlation with histological injury scores as defined above. Administered tagged cells are readily detected in the microvasculature of ARF kidney but not in kidneys from sham animals or in their urine. By day 7 following infusion, the tagged cells appeared phenotypically unchanged. Additionally, there were no adverse effects that resulted from the administration of any cell type in sham or ARF animals, likely because these were autologous (from the animal or potentially the patient who is treated for ARF) or "syngeneic" cells (from the animal's litter mate or a HSC/MSC donor who is immune-compatible with the patient who is treated for ARF). Importantly, additional in vivo studies with allogeneic MSC demonstrated that these were well tolerated and exhibited renoprotective effects in rats with ARF that were identical to those obtained with syngeneic MSC.

The results from the experiments in the rat models will be applicable to the treatment of patients. In clinical practice, patients who qualify for this form of treatment, i.e., those with the severest form of ARF, one that carries a mortality of up to 100%, particularly when ARF develops in the setting of multi-organ failure, may serve as their own, autologous HSC, MSC, EC, or hemangioblast donors. Accordingly, bone marrow is aspirated under local anesthesia and under sterile conditions. HSC are isolated and enriched from the bone marrow aspirate using FACS and are subsequently cryopreserved until use.

Hemangioblasts are obtained form HSC by FACS sorting for CD 133. Highly pure MSC are generated in sterile culture of bone marrow aspirates, are cryopreserved until needed, or are pre-differentiated into EC and tubular cell precursors, and cryopreserved until needed. This autologous approach requires, however, that the patient who is in need of this form of treatment is able to survive for the number of days that are needed to harvest, enrich, culture expand, differentiate, etc. his/her own cells. Because of this time delay, the vast majority of patients with severe ARF or MOF will not be able to be treated with their own cells, unless these have been procured prior to the development of ARF or MOF. If not available, allogeneic MSC that are blood group compatible, in their undifferentiated state or after pre-differentiation into EC or tubular phenotype are administered as fist line treatment, exploiting their robust immunomodulating capacity. Subsequent SC or cell treatments may be repeated allogeneic MSC doses or autologous SC that have been procured from the patient in the mean time.

Additional studies will be conducted to determine whether the administration of a single cell type (see above), repeated administrations of a single cell type or cell combinations are more renoprotective. A particular focus in these experiments will be to determine if co-administered HSC and MSC represent a superior form of therapy for the specific conditions that are treated with the present invention (Example 2 below).

Example 2

Determine the Ratio of MSC and HSC for Co-Administration Therapy

Using as a guideline the approximate ratio of HSC and MSC numbers in the normal bone marrow, protocols in which the ratios or doses of co-administered HSC/MSC given to rats with ARF, models and animal strains as in Example 1, were varied.

The relative renoprotective potency of various SC treatment protocols was tested by infusing intravenously jugular, femoral or tail vein) or intra-arterially (into suprarenal aorta via carotid or femoral artery) HSC alone, MSC alone or HSC in combination with MSC at a HSC/MSC ratio of 1:1, 3:1, 5:1 or 8:1 to rats immediately after induction of severe or modest ARF as well as infusion of HSC alone, MSC alone or HSC/MSC in ratios of 1:1, 3:1, 5:1 or 8:1 24 hrs after induction of severe or modest ARF in rats (see above). The total number of cells administered in all studies was about $10^5$ to $10^6$ cells/animal.

Renal function, histological studies and outcomes in the experimental models were monitored as detailed in Example 1 above.

The following observations from the experiments using the rat model of ARF were made. Outcome is greatly improved when HSC/MSC are administered in combination at an average HSC/MSC ratio of 5:1. Animal mortality was abolished with the combination treatment. In comparison, HSC or MSC given individually provide a modest to good renoprotective effect. Stem cell homing, subsequent engraftment and gradual differentiation and integration into the ARF kidney occurred with much greater efficiency when HSC and MSC were co-administered, likely explaining the excellent organ repair and functional recovery that is obtained. Additionally, there were no adverse effects that resulted from the administration of HSC, MSC or both together.

Additional studies will be conducted to optimize co-administration protocols, including using different ratios of stem cells, including allogeneic stem cells, and to further identify and augment intrarenal homing and differentiation signals.

The results from the experiments in the rat model will be applicable to the treatment of patients. In clinical practice, patients who qualify for this form of treatment, i.e., those with the severest form of ARF, one that carries a mortality of up to 100%, particularly when ARF develops in the setting of multi-organ failure, will serve as their own, time permitting, autologous HSC/MSC donors. Bone marrow is aspirated under local anesthesia and under sterile conditions. HSC are isolated and enriched from the bone marrow aspirate using FACS and are subsequently cryopreserved until use. Highly pure MSC are generated in sterile culture of bone marrow aspirates. Appropriate numbers of HSC and MSC are combined at a defined ratio, e.g., 5:1, suspended in sterile saline or McCoy' solution, and administered into a large central vein. The latter access is always established in this group of patients. Unless contraindicated, a suprarenal aortic route of administration may prove superior, and can be routinely accomplished by cannulating a femoral artery and advancing the tip of the infusion catheter to an intra-aortic location well above the renal arteries. This route of administration allows the most direct and SC dose-sparing delivery of HSC/MSC into both renal arteries and thus into both kidneys. Studies in which the therapeutic results that are obtained with the intravenous infusion route (superior vena cava) are compared with those obtained using the intra-aortic route will establish which approach is superior. It is also important to note that, if needed, treatments with autologous HSC/MSC can be repeated. And, HSC and MSC from the donor of a kidney whose tissue type is close enough to that of the recipient and thus permits a successful allogeneic transplant, thereby requiring no or only modest immunosuppresive therapy, may also be administered at the time of or following the kidney transplant, for the treatment of EGD, respectively. Importantly and as detailed in Example 1, allogeneic MSC or their derivatives may be co-administered with autologous HSC, since the latter can be procured more quickly.

Example 3

Determine the Relative Potency for Wound Healing of HSC, MSC, Precursor Vascular Endothelial or Tubular Cells Derived from MSC by Pre-Differentiation, Hemangioblasts, of Fully Differentiated Vascular Endothelial Cells, and Define the Optimal Ratio of MSC and HSC for Co-Administration for Wound Healing The administration of individual cell types, as above, or MSC and HSC mixes to rats with ARF resulted in improved outcome (see above). Also, the abdominal, well-healed incision initially created for the induction of ARF (clamping of both renal arteries), contained large numbers (~40%) of tagged MSC and HSC-derived vascular and other cells, indicating that MSCs and HSCs can powerfully support the process of wound healing that includes angiogenesis. Further studies in animals with experimental abdominal wound infections alone or in the setting of LPS-induced shock with MOF, or in rats with combined ischemic ARF and cecal perforation-induced peritonitis/sepsis will examine whether cell therapy, as defined above, improves wound healing and related outcomes (see Example 4).

Example 4

Determine Stem Cell Therapy Protocols for Multi-Organ Failure

Stem cell therapies will be investigated that may effectively boost the body's ability to cope with the many deleterious consequences of multi-organ failure and to carry out repair and functional recovery of multiple organs rather than that of a single one such as the kidney with ARF. The multi-organ failure models that will be used is the endotoxin model in mice, in which endotoxin from gram negative bacteria (LPS) is injected, resulting in many manifestations of clinical multi-organ failure, including ARF. Another model of MOF in rats or mice combines ischemic ARF and cecal perforation-induced peritonitis/sepsis, shown to most optimally reproduce the manifestations of clinical MOF. Besides improvement in organ function, successful MSC and HSC therapy is expected to reduce the 100% mortality seen in experimental multi-organ failure, and to significantly enhance wound repair, when applicable (see Example 3 above).

Example 5

Determine MSC, HSC, and EC Therapy for Generalized Microchimerism

Interventions to establish generalized microchimerism in order to induce increased immune tolerance of the transplanted kidney or other organs, i.e., reduced rejection rates, will be examined using suitable rat and mouse kidney transplant models, and employing autologous and allogeneic donor and recipient combinations. The HSC and/or MSC will be administered alone or in various ratios. HSC/MSC pre-differentiated in vitro or hemangioblasts will also be administered in separate experiments. The degree of microchimerism is determined by identification of tagged donor cells in the circulation, bone marrow and kidney, when applicable. The degree of graft acceptance or tolerance is tested in animals with allogeneic transplants by tapering or discontinuing antirejection medications. Animals with microchimerism are expected to exhibit lower rejection rates than those without. MSC and EC may also be used to establish a state of "microchimerism". The unique immunomodulating effects of allogeneic MSC and EC precursors that are derived from MSC, as above, may prove particularly beneficial for the management of TA-ARF or EGD and for the boosting of graft survival for transplanted organ in general.

Example 6

Determine MSC, HSC, and EC Therapy for "Renovascular Microchimerism"

Interventions to establish "renovascular microchimerism" in order to induce increased immune tolerance of the transplanted kidney, i.e., reduced rejection rates, will be examined using suitable rat and mouse kidney transplant models, and employing autologous and allogeneic donor and recipient combinations. The HSC and MSC will be co-administered in various ratios. HSC/MSC pre-differentiated in vitro, hemangioblasts, or EC or combination thereof will also be administered. The degree of microchimerism is determined by identification of tagged donor cells in the circulation, bone marrow and kidney vasculature. The postulated degree of enhanced graft tolerance as a function of "renovascular microchimerism" is assessed as in Example 5 above. The unique immunomodulating effects of allogeneic MSC and EC precursors that are derived from MSC, as above, may prove particularly beneficial for the management of TA-ARF or EGD and for the boosting of graft survival or tolerance.

Example 7

Determine Therapeutic Effectiveness of Hemangioblasts in ARF and MOF

Following the experimental design protocols detailed above, hemangioblasts isolated from bone marrow harvested, FACS enriched HSC will be administered to prevent or treat ARF (native kidneys, transplanted kidney) and multi-organ failure. The very high potential of these cells to differentiate into vascular endothelial cells may prove to be particularly advantageous when renovascular or generalized vascular injury predominates in a particular phase of ARF of multi-organ failure. Results obtained with hemangioblasts will be compared to those obtained with protocols detailed in the preceding Examples.

Example 8

Examine the Effect of Hematopoietic Stem Cell Mobilization on the Outcome of Ischemia/Reperfusion-Induced ARF in Rats and Mice Ischemic ARF will be induced in anesthetized, adult rats and FVB mice by timed clamping of both renal pedicles and in rats as above. Renal function, histological changes, overall outcome will be monitored as above. Since stem cell mobilization with cytoxan, followed by G-CSF maximally increases both HSC and neutrophils in the circulation, and since this protocol causes a marked increase in the mortality of animals with ARF, such an approach must be avoided clinically. However, HSC mobilization with erythropoietin and other factors is not associated with a significant rise in peripheral neutrophil numbers, which suggests that such a form of stem cell mobilization may be renoprotective in ARF, TA-ARF and MOF.

Example 9

Characterization of Homing Signals and Mechanisms for Stem and MSC-Derived Cells in the Kidney with ARF The kidneys and HSC, MSC, EC (precursors from MSC, mature EC), and hemangioblasts from the animals studied in Examples 1 and 2 will be further examined for SDF-1 and CXCR4 expression using in situ hybridization, real time PCR, and immuno-histo- and cyto-chemistry. The importance of the chemokine SDF-1 alpha, its beta splice variant, and its receptor CXCR4 in mediating chemokinesis of HSC/ MSC and other cells will be investigated in vitro using transwell migration assays and in proof of principle experiments with neutralizing anti-SDF-1 or anti-CXCR4 antibodies. The effect of administered neutralizing anti-CXCR4 antibodies on the homing efficiency of tagged HSC and MSC in the ARF kidney will be assessed.

Determinations will be made to corroborate that injured tubular or endothelial cells in ARF express SDF-1 (alpha or beta), and whether mobilized stem cells express CXCR4. This determination will provide for a system for mediation of homing of CXCR4-expressing stem cells towards the sites of nephron and vascular injury. Homing efficiency of the HSC/ MSC/EC and hemangioblasts will be optimized to improve the renoprotective and organ protective stem cell therapies.

Example 10

Determine the Effect of HSC or MSC Therapy on the Outcome of ARF in Mice

In order to determine whether HSC or MSC home into the kidney in ARF, and whether they transdifferentiate, integrate and act renoprotectively, genetically marked, phenotyped cells will be exogenously administered and traced in the kidney of mice with ARF. HSC or MSC will be obtained from the femurs of eGFP transgenic FVB mice that express enhanced green fluorescent protein (eGFP+ HSC). The eGFP+ HSC will, if necessary, be further enriched by FACS sorting (c-kit, sca-1, lin negative), eGFP+ MSC are clonally expanded, and administered intravenously to wild type mice with ARF as described in Examples 1 and 2 above. Appropriate controls will be included. At defined time points following induction of ARF, kidneys from experimental and control mice will be examined in order to assess where eGFP cells are located and whether they have transdifferentiated into renal tubular or endothelial cells, respectively. Renal function and histology is examined as above and for direct tissue evidence of transdifferentiation and integration of eGFP+ cells into tubular or vascular endothelial sites at which ARF caused cell injury and loss. The paracrine potential of HSC and MSC to produce, deliver and release renoprotective growth factors and cytokines in situ (e.g. HGF, EGF, IGF-I, VEGF, NOS, and others) will be tested in in vitro studies using ELISA and other suitable assays and real time-PCR. In vivo studies with neutralizing antibodies to growth factors and cytokines or their respective receptors or inhibitors of NOS will be used to test the importance of these factors as mediators of renoprotection and repair.

Example 11

Determine the Effect of MSC Therapy on Outcome of ARF in Mice

MSCs originate, like the kidneys, from the mesoderm and have been shown to transdifferentiate into numerous cell types. MSC from eGFP transgenic FVB mice will be utilized. The eGFP+ MSC will be isolated from harvested bone marrow based on their characteristic and selective attachment to the culture dish. A functional MSC culture system will be established that provides for well maintained eGFP expressing MSCs at later passages. Cultured eGFP+ MSC will be administered to wild type mice with ARF as described in above Examples and outcome and tissue analyses will be performed as above. The results will be analyzed to determine the MSC renoprotective effects as compared to the HSC renoprotective effects. The results may suggest that co-administration of HSC and MSC may be most beneficial, since these cells depend on each other for effective hematopoiesis. The paracrine potential of MSC to produce, deliver and release renoprotective growth factors in situ including HGF, EGF, IGF-I, etc. will be tested in in vitro and in vivo studies as described in Example 10.

Example 12

Assess the Effect of MSC Therapy on the Function of Renovascular Endothelial Cells in ARF The kidney is a highly perfused organ, receiving 20% of the cardiac output, and the complexity of the intrarenal circulation facilitates the processes of filtration and tubular transport. It is now recognized that vascular endothelial cell dysfunction and death are important determinants of loss of renal function in ARF. The bone marrow contains endothelial precursor cells (CEP, circulating endothelial precursors), that can be mobilized into the peripheral circulation, from where they can contribute to wound healing or participate in tumor angiogenesis. Both bone marrow-derived stem cells types, HSC and MSC, are able to transdifferentiate into endothelial cells. The effect of MSC will be tested, after transdifferentiation into endothelial cells, or c-kit+/VEGFR2+ hematopoietic cells, from eGFP transgenic mice, on the course of ARF. The cell type that will be assessed in these experiments is the postglomerular vascular endothelial cell that is injured or killed in ARF.

MSC and c-kit+/VEGFR2+ hematopoietic cells from eGFP transgenic mice (CEP) will be subjected to various transdifferentiation protocols in vitro with the goal of obtaining endothelial cells, phenotypically confirmed by appropriate endothelial cell markers. Cells will then be administered to mice with ARF as in the preceding protocols (Examples 1 and 2) and their impact on the course of ARF will be monitored as above. Kidney tissues will be examined for location of administered stem cells and vascular integration.

Example 13

Examine the In vitro Transdifferentiation of MSC into Renal Tubular and Vascular Endothelial Cells Spontaneous transdifferentiation of MSC generally does not occur. Treatment of MSC cultures with specific factors results in their transdifferentiation into adipocytes, osteocytes, chondrocytes and other cell types. Differentiation factors will be identified that result in transdifferentiation of MSC into tubular cells. The kidney is of mesodermal origin and during embryonal nephrogenesis ureteric bud cells induce a mesenchymal-epithelial transdifferentiation in the metanephric mesenchyme. This process is influenced by several growth factors (HGF, EGF, LIF, TGF alpha, FGF2) that exhibit redundancy and is critical to overall nephrogenesis, since failure of induction of the metanephric mesenchyme results in its apoptosis, and since the mesenchyme, on the other hand, induces the ureteric bud to undergo branching morphogenesis which results in collecting duct formation. MSCs will be examined to determine their ability to transdifferentiate into tubular epithelial cells.

Cell culture systems optimized for MSC, including plating of cells on collagen (I or IV) and/or fibronectin, exposure to differentiation factors such as VEGF and others, co-culture systems with target cells, conditioned media from target cells, are used in these studies. The capacity of various culture conditions, differentiation and growth factors to induce the transdifferentiation of MSC into renal vascular endothelial cells and tubular progenitor cells will be examined. EC may be generated in vitro from HSC or MSC by differentiation. For example, MSC may be grown and differentiated in culture, followed by injury, for example by scraping or ATP depletion. Additional MSC added to the injured target cells with conditioned media and the MSC then become EC which may be used for administration. Tubular cells may be generated by the same injury model.

Pax-2 will be used as an initial marker of tubular cell induction, since it is a kidney specific transcription factor that is expressed in the embryonic kidney, and that, importantly, is re-expressed in proximal tubular cells that are injured in ARF. Megalin or aquaporin-1 are markers of proximal tubular cells. PECAM-1 (CD34), von Willebrandt Factor, dil-ac-LDL uptake, eNOS, VEGF-Receptor 2, and others are suitable markers of EC phenotype.

The in vitro systems for induction of MSC into tubular or endothelial cells will then be used for further analysis of molecular mediator signals and their utility for pre-differentiation of MSC into these cell types that may be subsequently tested in ARF treatment protocols, as detailed above.

For in vitro differentiation of MSC into EC, MSC may be plated onto Matrigel® using techniques known to one of skill in the art (available from BD Biosciences, Franklin Lakes, N.J.).

Example 14

Analyze In vivo Transdifferentiation and Integration of Intrarenally Injected MSC (Subcapsular, Cortical Interstitium) and HSC in Intact and ARF Kidneys in Mice HSC and MSC from eGFP transgenic mice will be injected (subcapsular or in mid cortex) into normal and ARF kidneys of wild type mice. Their potential transdifferentiation and integration into tubular and vascular structures will be analyzed histologically, using appropriate differentiation markers as above. The data from these in vivo studies will determine whether MSC and/or HSC are able to transdifferentiate in vivo into specific renal cell types and the location of the injected cells. The influence of preexisting injury due to ARF on these processes will be assessed, and the influence of spontaneously or experimentally increased SDF-1 levels at the sites of injury on SC homing is determined.

Example 15

Analyze the Effects of HSC, MSC, Precursor Cells (EC, Tubular Cells), Hemangioblasts and Combinations Thereof on Kidney Function in Animals with Underlying Chronic Renal Failure or Chronic Kidney Disease Per Se or Superimposed ARF The effects of HSC and/or MSC and other defined cell treatments, as above, on the course of CRF (CKD) is examined in a progressive rat model with CRF, induced by $\frac{5}{6}^{th}$ nephrectomy or unilateral nephrectomy and contralateral, selective renal artery branch ligation. In addition, these cell therapies are also tested in a transgenic mouse model of type II diabetes mellitus (db/db strain) that develops progressive diabetic nephropathy and CRF is examined. Outcomes over time (renal function, urinary protein excretion, blood pressure, survival, and kidney histology) are examined as above in experimental and control animals.

The effects of SC treatment protocols tested in ARF or MOF models (models without underlying renal disease) (see Examples above) on the outcome of rats and mice with underlying CRF, induced surgically in rats or in transgenic db/db mice, will be analyzed in order to see whether stem cell therapy is effective in these high risk for ARF models, a clinically highly relevant issue.

Example 16

Analyze the Effect of genetically altered MSC in animals with ARF, TA-ARF, MOF and CRF It will be tested whether in vitro induced changes (by transfection) in the expression of renoprotective growth factors, cytokines, hemodynamic mediators, anti-inflammatory, anti-thrombotic or harmful cytokines or their receptors in MSC prior to their administration to animals with ARF can be used to boost the renoprotective potency of these cells. Genes of these humorally acting factors may be placed under the control of drugs, allowing for regulated expression or suppression of such cytokines. Outcomes will be tested as in the above Examples.

Example 17

Analyze the Effect HSC on Kidney Allograft Function

The effect of HSC, MSC and/or stem cell mobilization treatments on short- and long-term kidney allograft function will be analyzed. Kidney transplantation will be performed using a two-step rat model. The donor will be a Fisher 344, male rat, transgenic for human placental alkaline phosphatase. The recipient will be a compatible Fisher 344 female wild type rat or an incompatible Lewis female wild type rat. Function and outcome studies will be performed as described above using the kidney allograft rat model.

Although the invention herein has been described in connection with preferred embodiments thereof, it will be appreciated by those skilled in the art that additions, modifications, substitutions, and deletions not specifically described may be made without departing from the spirit and scope of the invention as defined in the appended claims. It is therefore intended that the foregoing detailed description be regarded as illustrative rather than limiting, and that it be understood that it is the following claims, including all equivalents, that are intended to define the spirit and scope of this invention.

The invention claimed is:

1. A method of treating acute renal failure, comprising delivering a single biologically and physiologically compatible solution containing a therapeutic amount of isolated human mesenchymal stem cells to a patient in need thereof, wherein the solution is not enriched for human pluripotent hematopoietic stem cells, wherein the therapeutic amount of human mesenchymal stem cells is between about 0.01 to about $5 \times 10^6$ mesenchymal stem cells per kilogram of patient weight, wherein the human mesenchymal stem cells are not co-administered with hematopoietic stem cells, wherein the patient suffers from or is at high risk of suffering from an acute deterioration in renal excretory function and wherein the mesenchymal stem cells are expanded in vitro to produce an enriched population of mesenchymal stem cells.

2. The method of claim 1 wherein said isolated mesenchymal stem cells comprise non-transformed stem cells.

3. The method of claim 1 wherein said isolated mesenchymal stem cells comprise genetically modified stem cells, wherein protective potency of said cells is augmented by genetic modification prior to administration in a patient in need thereof.

4. The method of claim 1 wherein said isolated mesenchymal stem cells comprise autologous cells.

5. The method of claim 1 wherein said isolated mesenchymal stem cells comprise allogeneic cells.

6. The method of claim 1, wherein the mesenchymal stem cells are isolated from bone marrow aspirates and adhere to the bottom of a culture dish while substantially all other cell types remain in suspension.

* * * * *

UNITED STATES PATENT AND TRADEMARK OFFICE
CERTIFICATE OF CORRECTION

PATENT NO. : 8,603,462 B2
APPLICATION NO. : 10/551317
DATED : December 10, 2013
INVENTOR(S) : Christof Westenfelder It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1805 days.

Signed and Sealed this
Twenty-third Day of May, 2017

Michelle K. Lee
*Director of the United States Patent and Trademark Office*